United States Patent [19]

Ovassapian et al.

[11] Patent Number: 5,024,218
[45] Date of Patent: Jun. 18, 1991

[54] INTUBATING AIRWAY

[75] Inventors: Andranik Ovassapian, Northbrook; John F. Dye, Elgin, both of Ill.

[73] Assignee: The Kendall Company, Mansfield, Mass.

[21] Appl. No.: 266,284

[22] Filed: Oct. 27, 1988

Related U.S. Application Data

[63] Continuation-in-part of Ser. No. 112,004, Oct. 21, 1987, abandoned, Continuation of Ser. No. 848,677, Apr. 4, 1986, abandoned.

[51] Int. Cl.⁵ .............................................. A61M 16/00
[52] U.S. Cl. .............................. 128/200.26; 128/207 M
[58] Field of Search ............... 128/200.26, 207.14, 128/3, 10, 11, 12, 13, 15, 16, 20, 136, 207.15, 207.17, DIG. 26, 859, 657, 772; 604/174, 178

[56] References Cited

U.S. PATENT DOCUMENTS

| | | | |
|---|---|---|---|
| 2,756,742 | 7/1956 | Barton | 128/207.14 |
| 3,146,776 | 9/1964 | Duncan | 128/12 |
| 3,153,267 | 10/1964 | Rowland, Jr. | 128/16 |
| 3,756,244 | 9/1973 | Kinnear et al. | 128/207.14 |
| 3,774,616 | 11/1973 | White et al. | 128/200.26 |
| 4,054,135 | 10/1977 | Berman | 128/200.26 |
| 4,148,308 | 4/1979 | Sayer | 128/207.14 |
| 4,198,970 | 4/1980 | Luomanen | 128/207.15 |
| 4,425,911 | 4/1984 | Luomanen et al. | 128/200.26 |
| 4,553,540 | 11/1985 | Straith | 128/207.14 |
| 4,576,187 | 4/1971 | Oddera | 128/207.14 |
| 4,727,872 | 3/1988 | Hawk | 128/207.14 |
| 4,793,327 | 12/1988 | Frankel | 128/207.14 |
| 4,848,331 | 7/1989 | Northway-Meyer | 128/207.14 |
| 4,850,371 | 7/1989 | Broadhurst et al. | 128/719 |
| 4,877,021 | 10/1989 | Higer et al. | 128/207.14 |
| 4,896,667 | 1/1990 | Magnuson et al. | 128/207.14 |

FOREIGN PATENT DOCUMENTS 799845 8/1958 United Kingdom ........... 128/207.14

Primary Examiner—Randall L. Green
Assistant Examiner—K. M. Reichle
Attorney, Agent, or Firm—Alvin Isaacs

[57] ABSTRACT

An intubating airway having an elongated body comprising a lingual flat portion with a transversely disposed faceplate on one end. The other end comprises a curved surface which tapers to a narrow distal edge. A pair of flexible guide walls are upstanding from said flat lingual portion, to define a generally tubular guideway. Outwardly of the flexible walls are a pair of upstanding walls which attach to said faceplate, to provide a blocking arrangement for a patient's teeth, insuring protection for any medical instrument disposed within said flexible guide.

4 Claims, 1 Drawing Sheet

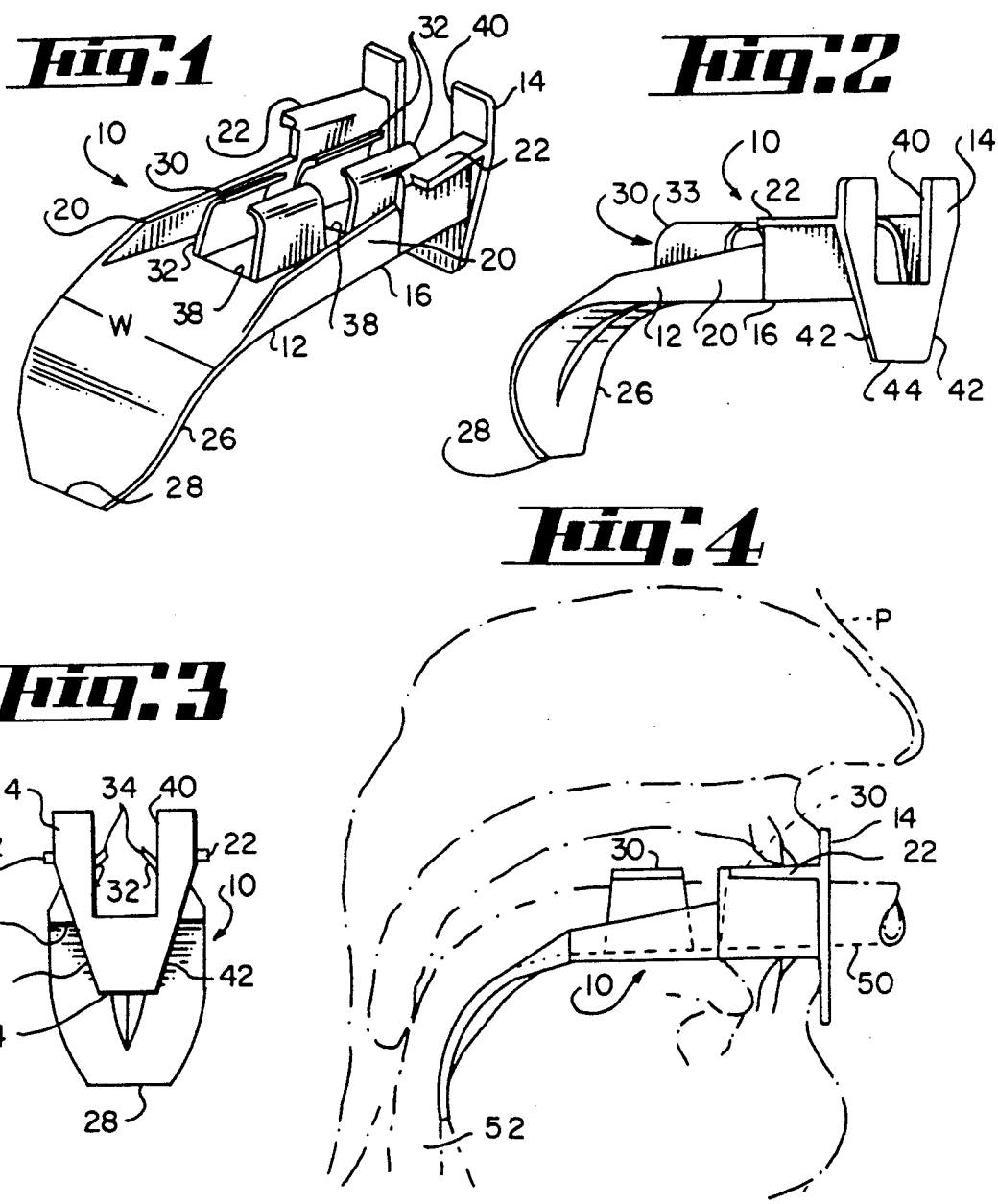

INTUBATING AIRWAY

This is a continuation-in-part of application Ser. No. 112,004 filed on Oct. 21, 1987, now abandoned. That application is a continuation of application Ser. No. 848,677, filed Apr. 4, 1986, now abandoned.

BACKGROUND OF THE INVENTION

1. Field of the Invention

The present invention relates to oral airways wherein devices are adapted to function as a guide and a passageway for medical devices such as an endotracheal tube for the intubation of a human larynx and trachea.

2. Prior Art

For maintenance of a safe general anesthesia, often it is necessary to intubate the trachea of the patient to permit the safe passage of oxygen and anesthesia gases into and out of the lungs of the patient. Airways are also utilized to prevent the patient's tongue from falling back into the throat and obstructing the flow of air into the lungs, as for example, in an unconscious patient and when an anesthetic is being administered to the patient. When using the intubating airway for fiberoptic intubation, it is also necessary, to insert a suction catheter into the patient's pharynx for removal of phlegm, blood, saliva, etc.

Prior art airways may be seen as, for example, in U.S. Pat. No. 4,198,970 wherein a plurality of channels are arranged in a side-by-side relationship, in an airway device. While this device may permit simultaneous administering of anesthetics, oxygen, and suctioning, it does not provide a passageway and guide for an endotracheal tube on its uppermost portion thereof. Another airway intubator, is shown in U.S. Pat. No. 4,338,930 wherein the intubating airway is of a tube-like construction to permit an endotracheal tube to be inserted into a human larynx, blindly, use of a fiberscope would be difficult with this device. A further airway is shown in U.S. Pat. No. 4,553,540 wherein the airway has an upper and lower portions which are hingedly connected together for articulation therebetween. This is a rather complicated device which does not permit the passage of an endotracheal tube while maintaining the intubating airway in place. Other U.S. patents which show different oropharyngeal airways include: U.S. Pat. Nos. 4,054,135; 4,363,320; 4,069,820; 4,068,658; 3,756,244; and 3,419,004.

BRIEF SUMMARY OF THE INVENTION

The oropharyngeal airway of the present invention is adapted to facilitate tracheal intubation of a flexible fiberoptic endoscope in both awake and anesthetized patients.

The airway is designed to protect the fiberoptic endoscope from damage by the patient's teeth, and to maintain itself in a midline position.

This airway may be made from many suitable medical materials and has a generally elongated body having a proximal end and a distal end transversely disposed faceplate at its proximal end. The distal end of the elongated body comprises a generally curved lingual portion which is somewhat wider at its point of conjuncture with the proximal half of the elongated body, narrowing down and becoming flat at its distalmost end of the distal half of the airway. The lingual portion comprises a generally 90° curve so as to permit an endotracheal tube and fiberscope to be directed towards the patient's larynx. The airway has a pair of upstanding sides on its proximal end extending anteriorly from the faceplate. The upper portion of the upstanding walls each have a outwardly extending flange which itself is also attached to the faceplate. The outwardly extending flanges are used as a stop for the patient's teeth. Thus, any device inserted within the airway will be protected thereby. The lingual surface of the proximal half of the airway has a plurality of curved guide walls extending upwardly away therefrom. Each guide wall is curved at its distalmost end towards its associated guide wall, having a space thereinbetween, however. Each guide wall is flexible so as to permit the removal of the airway from a patient, after a medical device has been inserted thereby.

The intubating airway is designed to accommodate an endotracheal tube while being directed to the larynx and trachea with the help of a flexible fiberoptic endoscope. This airway thus provides adequate oropharyngeal space for mask ventilation before tracheal intubation.

Due to the generally flat nature of the airway, suctioning of the mouth is possible when the airway is in place, with the patient lying on his back or sitting up.

The airway has a wide lingual surface to keep the patient's tongue away from the oropharynx. The airway has an open and flat surface on its distal end, permitting easy maneuvering of a fiberscope tip, both in the anterior-posterior plane and the lateral plane, a capability not realized by other airways.

BRIEF DESCRIPTION OF THE DRAWINGS

The objects and the advantages of the present invention will become more apparent, when viewed in conjunction with the following drawings, in which:

FIG. 1 is a perspective view of the airway according to the present invention;

FIG. 2 is another perspective view of the airway;

FIG. 3 is a view looking towards the proximal end of the airway; and

FIG. 4 is an elevational view of the airway within a patient's mouth.

DESCRIPTION OF THE PREFERRED EMBODIMENTS

Referring now to the drawings in detail and particularly to FIG. 1, there is shown an oropharyngeal airway 10 having an elongated body 12 and a transversely disposed faceplate 14 arranged on its proximal or first end and a distal end having a distalmost edge 28. The airway 10 may be constructed from any suitable material, such as plastic or metal. The airway 10 may also be made in different sizes to accommodate children, etc.

The airway 10 has a generally flat lingual surface 16 on the proximal half thereof, which minimizes movement of the airway 10. An upstanding wall 20 extends from each side of the lingual surface 16, and is secured to the back-side of the faceplate 14, as shown in FIGS. 1 and 2. Each wall 20 has a narrow outwardly directed side flange 22 disposed along a portion of its distalmost edge adjacent the faceplate. Each wall 20 tapers in height down to the lingual surface 16 from the respective side flanges 22. The elongated body 12 of the airway 10 is generally at its widest at this location marked "W" in FIG. 1 which is the lingual surface, to keep the patient's tongue away from his oropharynx. The airway 10 has a distal portion 26 which curves about 90° away from the lingual surface 16 and tapered towards its distalmost edge 28 which is its second or other end, to permit placement thereof between a patient's maxillary and mandibular molars. The widened half (flatter portions) of the airway 10 prevents the tongue and soft tissue and soft tissues of the anterior pharyngeal wall from falling back and obstructing the view of the epiglottis and larynx.

An arrangement of resilient guide means 30 are disposed on the upper or top side of the lingual surface 16. The guide means 30 comprise a pair of flexible upstanding walls 32, which extend longitudinally along at least part of the elongated body 12 and are spaced apart from one another, and face one another, each wall 32 having an uppermost distal edge 34 which is curved towards its adjacent wall 32. A space or gap or opening is disposed between opposite edge 34 of the walls 32 as shown in FIGS. 1 and 3. This opening or gap permits the separation of a medical device such as an endotracheal tube, from the airway 10 while the endotracheal tube remains in a patient to permit the removal of the airway 10 from the patient.

The lingual surface 16, has an opening 38 therethrough, between each pair of spaced walls 32, as most easily seen in FIG. 1.

The faceplate 14, shown most clearly in FIG. 3, has a U-shaped opening 40 across its middle uppermost portion. The faceplate 14 has a pair of side edges 42 which taper towards one another and end at a truncated bottom edge 44.

The view shown in FIG. 4, indicates that the airway 10 provides an open space both laterally and in the anterior-posterior planes in the oropharynx. A medical instrument 50, such as flexible fiberoptic endoscope or endotracheal tube is disposed in the opening 40 of the faceplate 14, between successive pairs of guide means 30, which define a palatal surface. Because the palatal surface (the curved upper portions of the guide means 30) does not continue to the distal end of the airway 10, an open space is provided so that the tip 52 of the medical instrument 50, such as a fiberoptic endoscope can be manipulated and directed in either the lateral or anterior-posterior planes. The instrument 50 shown in FIG. 4 is depicted as inserted into the pharynx ph of the patient "P" therembodied.

The airway 10 has a generally tubular passageway defined by the flexible walls 32 on its proximal portion so as to permit a tubular medical instrument to pass readily therethrough. This tubular section, the portion between the curved flexible walls 32, is capable of being opened at the top or spread apart to increase the width of the opening between walls 32, so that any instrument 50 may be released therefrom, thus permitting the airway 10 to be removed from a patient's mouth, if so desired, while leaving the instrument 50 in place. More specifically, the airway 10 guides both the endotracheal tube and an endoscope into position in the patient's bronchial tube and down the patient's throat. The endotracheal tube is fed onto the endoscope. The endoscope becomes a guiding device because it can be manipulated in the lateral and the posterior-anterior planes. Once the endotracheal tube is properly fed into the patient's airway and not the patient's esophagus, the endoscope may then be removed from inside of the endotracheal tube. The airway 10 may next then be removed from the patient's mouth by pulling the airway 10 our of the patient's mouth, then by spreading apart the flexible walls 32 further than in the relaxed unbiased position, the airway 10 may be removed from its place surrounding the endotracheal tube, leaving the endotracheal tube by itself in the patient's mouth and throat.

The intubating airway 10 is arranged to accommodate an endotracheal tube while being directed into the larynx l and trachea with the help of a flexible fiberoptic endoscope. This airway 10 provides adequate oropharyngeal space for mask ventilation before tracheal intubation. The faceplate 14 on the proximal end of the elongated body 12 of the airway 10 prevents the airway 10 from advancing too far into the mouth of patient, by abutting against the lips, teeth or gums, as shown in FIG. 4. The side flanges 22 provide a strike surface for the upper teeth of the patient, preventing damage to the instrument 50 carried thereadjacent.

Thus there has been shown an airway having means for permitting lateral and anterior-posterior guidance of a medical instrument, and allowing the removal of the airway from the patient, while leaving the medical instrument still in the patient's mouth, in manner not shown in the art.

The appended claims are intended to be interpreted in an exemplary and not in a limiting sense.

We claim:

1. An intubating airway adapted for insertion into the mouth of a patient, said airway comprising:
   an elongated body having opposed first and second ends and a longitudinal axis extending therebetween;
   a generally flat section adjacent to said first end;
   faceplate means, transversely disposed across said first end of said body, for abutting against the lips, teeth or gums whereby to prevent said second end from advancing too far into the mouth;
   curved, generally tongue-shaped portion means adjacent said second end, said curved portion means for permitting placement of said airway between the patient's maxillary and mandibular molars; and
   flexible guide means for allowing insertion of a medical instrument in or removal of the instrument from said airway in a first, flexed, biased position but normally being in a second, relaxed, unbiased position, said guide means comprising at least one pair of opposed walls upstanding from only said flat section and extending longitudinally down said flat section, said walls being spaced apart and each said wall having an uppermost distal edge which is curved towards the opposed said wall, said distal edges being spaced apart whereby said edges may be flexed further apart to facilitate said insertion or said removal of the medical instrument within said airway.

2. An airway as defined in claim 1 wherein said second end is a generally flat end open for permitting manipulation of the tip of a medical instrument when inserted thereon.

3. An airway as defined in claim 1 wherein said guide means further includes a second pair of said upstanding walls also extending along said flat section adjacent said first end and being attached to said faceplate.

4. An intubating airway for insertion into the mouth of a patient, said airway comprising:
   an elongated body having generally flat first and second ends and a longitudinal axis extending therebetween;
   curved, generally tongue-shaped portion means adjacent said second end, said curved portion means for permitting placement of said airway between the patient's maxillary and mandibular molars; and flexible guide means for allowing insertion of a medical instrument in or removal of the instrument from said airway in a first, flexed, biased position but normally being in a second, relaxed, unbiased position, said guide means comprising at least one pair of opposed walls upstanding from only said first flat end and extending longitudinally down said first flat end, said walls being spaced apart and each said wall having an uppermost distal edge which is curved towards the opposed said wall, said distal edges being spaced apart whereby said edges may be flexed further apart to facilitate said insertion or said removal of the medical instrument within airway.

* * * * *